United States Patent [19]

Ledley

[11] 4,005,311
[45] Jan. 25, 1977

[54] DIAGNOSTIC X-RAY SYSTEMS

[75] Inventor: Robert S. Ledley, Silver Spring, Md.

[73] Assignee: Georgetown University, Washington, D.C.

[22] Filed: Nov. 4, 1975

[21] Appl. No.: 628,708

Related U.S. Application Data

[63] Continuation-in-part of Ser. No. 443,042, Feb. 15, 1974, Pat. No. 3,922,552.

[52] U.S. Cl. .......................... 250/445 T; 250/221
[51] Int. Cl.² ...................................... G01N 21/34
[58] Field of Search .......... 250/445 T, 360, 358 T, 250/451, 456, 491, 505, 510, 221

[56] References Cited
UNITED STATES PATENTS

| | | | |
|---|---|---|---|
| 2,659,824 | 11/1953 | Burnham | 250/491 |
| 2,916,627 | 12/1959 | Rolke | 250/445 T |
| 3,629,594 | 12/1971 | Sandberg | 250/491 |
| 3,708,664 | 1/1973 | Bock et al. | 250/445 T |
| 3,733,487 | 5/1973 | Louche et al. | 250/445 T |
| 3,835,323 | 9/1974 | Kahil | 250/360 |

*Primary Examiner*—Davis L. Willis
*Attorney, Agent, or Firm*—Connolly and Hutz

[57] ABSTRACT

A shutter arrangement and activator device for a diagnostic X-ray machine of the type which rotates about the patient while scanning with thin beams for analysis by computers for storing and reconstructing the results in tangible form. The shutter mechanism is positioned between the X-ray source and a detector unit and includes a movable apertured shutter plate disposed between a pair of slotted plates. The shutter plate is automatically moved into and out of the X-ray path by means of a patient detector system. A belt or band, which permits the passage of X-rays but not light, is disposed on the patient and triggers the detector system.

18 Claims, 13 Drawing Figures

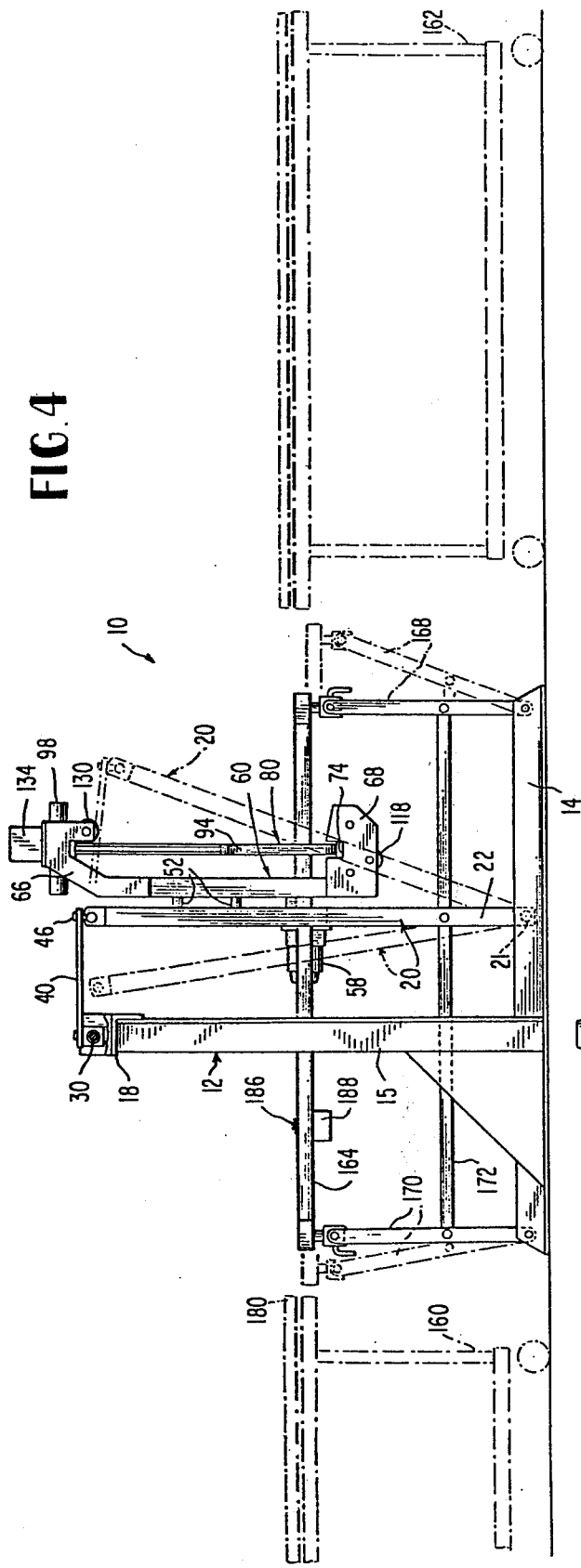
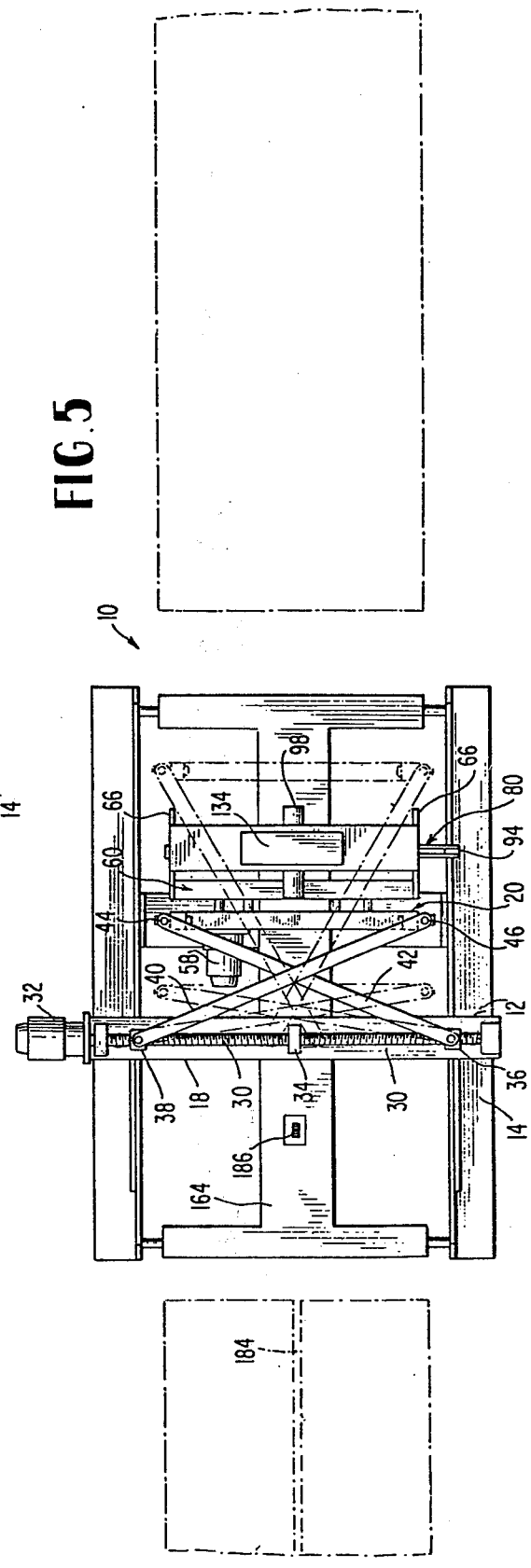

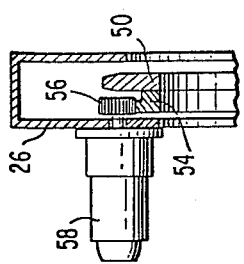
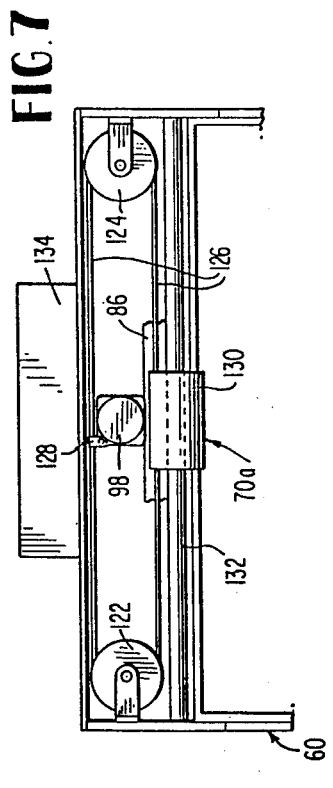
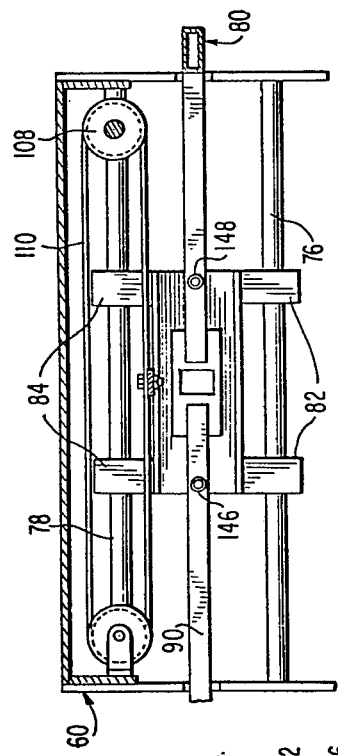
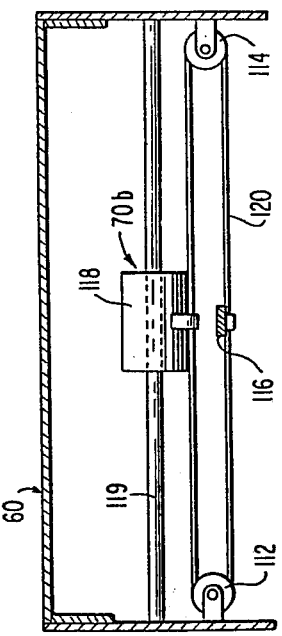
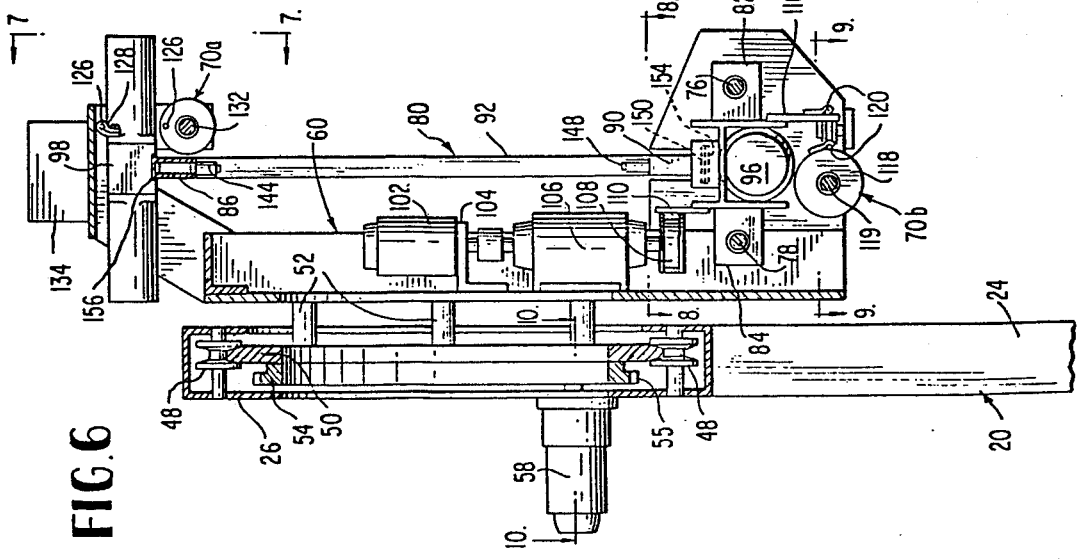

DIAGNOSTIC X-RAY SYSTEMS

This is a continuation-in-part application of my copending application Ser. No. 443,042, filed Feb. 15, 1974, entitled DIAGNOSTIC X-RAY SYSTEMS, now U.S. Pat. No. 3,922,552, issued Nov. 25, 1975.

This invention relates to improvements in diagnostic X-ray systems, and more particularly, to an improved shutter mechanism and automatic actuation means for such systems.

The concept of utilizing X-ray scanning with thin beams for analysis by computers for storing and reconstructing the results in tangible form is well known. Reference is made to U.S. Pat. No. 3,106,640 to Oldendorf; U.S. Pat. No. 3,591,806 to Brill, dated July 6, 1971; U.S. Pat. No. 3,499,146 to Richards, dated Mar. 3, 1970; and U.S. Pat. No. 3,778,614 to Hounsfield, dated Dec. 11, 1973. Each of these patents, at least in part, discloses a scanning technique wherein thin tomograhic slices or cross-sections of an organ of the human body are analyzed and thereafter presented in a manner which can be interpreted by a physician.

The concept of rotational scanning by X-rays for the reconstruction of planar anatomical sections goes back at least fifteen to twenty years (see, e.g., Kuhl, *Radiology*, Volume 71, page 875, 1958). Mechanical, electronic, and radiological technology to accomplish such procedures, while constantly improving in sophistication and cost-effectiveness, were adequate for the purpose. The principal difficulties impeding progress in the field were in the development of mathematical and computational algorithms to make the reduction of the voluminous data generated practicable. Concurrent research in this problem of reconstruction of a scalar field over a plane by means of linear projections was under way in the fields of radio astronomy (cf. Bracewell, *Austr. J. Physics*, Volume 9, page, 198, 1956) and electron microscopy (Klug, et al., Acta Cryst. Volume 11, page 199, 1958). By 1963, Cormack (J. Appl. Phys. Volume 34, page 2722, 1963) was sufficiently advanced that he could apply Fourier-transform methods in an experimental test using gamma radiation and a Geiger-counter detector.

In their review of reconstruction methods, Gordon and Herman (*Internatl. Rev. Cytol.*, 1973) divided the known algorithms into four categories: (1) Summation (dating back to the 1920's); (2) Fourier transforms (from 1955); (3) Analytic solutions of integral equations (from 1917) including the convolution method (1967); and (4) Series expansion (from 1937).

It is the principal objective of this invention to improve the state of the prior art in contributing a tomographic scanning instrument having a degree of efficiency, practicality and flexibility heretofore unknown.

Another principal objective of this invention is to provide a tomographic scanner having a capability of scanning any porton of the human body with equal efficiency and accuracy.

Another important objective of the invention is to provide a medical diagnostic apparatus of the type described in which the plane of the scanner can be tilted over a relatively wide range of attitudes.

The mechanism of this invention has means to rotate the scanning device while the scanning mechanism can be moved transversely after each partial rotation. This is common in tomographic photography. However, an important objective of this invention is to provide means wherein the translational scanning has an increased degree of adjustability. For instance, a 9 inch scan can be used for the head, arm, or leg, while a 15 inch to 20 inch scan may be necessary for the trunk of the body. The instant machine is readily adjustable for accomplishing either.

Another important objective of this invention is to provide an instrument wherein the rotational movement can be adjusted in degree increments from 1° to 6°. In other words, this objective of the invention can reduce radiation dose given to a particular patient by perhaps taking a scan at every 6° rather than at each degree. A further objective of the invention is to provide means to adjust the distance between transverse scans as determined by the medical requirements of the particular patient.

Another principal objective of this invention is to provide a shutter arrangement. This shutter arrangement obviates the necessity for water bags. This substantially increases the flexibility of use. Water bags, of course, create the possibility of breakage, thereby creating an extremely dangerous condition in view of the high-voltage electronic equipment associated with X-ray machines. The closest prior art of which the inventor is aware concerning the shutter arrangement is U.S. Pat. No. 3,835,323 to Kahil, entitled RADIATION INSPECTION APPARATUS WITH ADJUSTABLE SHUTTER FOR INSPECTING DIFFERENT SIZES OF TUBULAR GOODS, dated Sept. 10, 1974. The Kahil patent discloses a radiation inspection apparatus for use with tubular goods and it is in a totally different environment than the apparatus disclosed herein which is designed for use on humans. Further there are important structural differences between the shutter arrangement of this invention and the device disclosed in the Kahil patent.

Still another objective of this invention is to provide a patient detection system which automatically actuates the X-ray source or the interposed shutter mechanism. A belt, which passes X-rays but is opaque to light or at least translucent with respect to light, is worn by the patient and interrupts a photocell detector which in turn causes the energization of the shutter mechanism.

These and other objectives of the invention will become more apparent to those skilled in the art by reference to the following detailed description when viewed in light of the accompanying drawings wherein:

FIG. 4 is a side elevation;

FIG. 5 is a plan view;

FIG. 6 is a rear view;

FIG. 7 is a sectional view taken along the lines 7—7 of FIG. 6;

FIG. 8 is a sectional view taken along the lines 8—8 of FIG. 6;

FIG. 9 is a cross-sectional view taken along the lines 9—9 of FIG. 6;

FIG. 10 is an enlarged sectional view of one element of the machine; and

Figure 1:
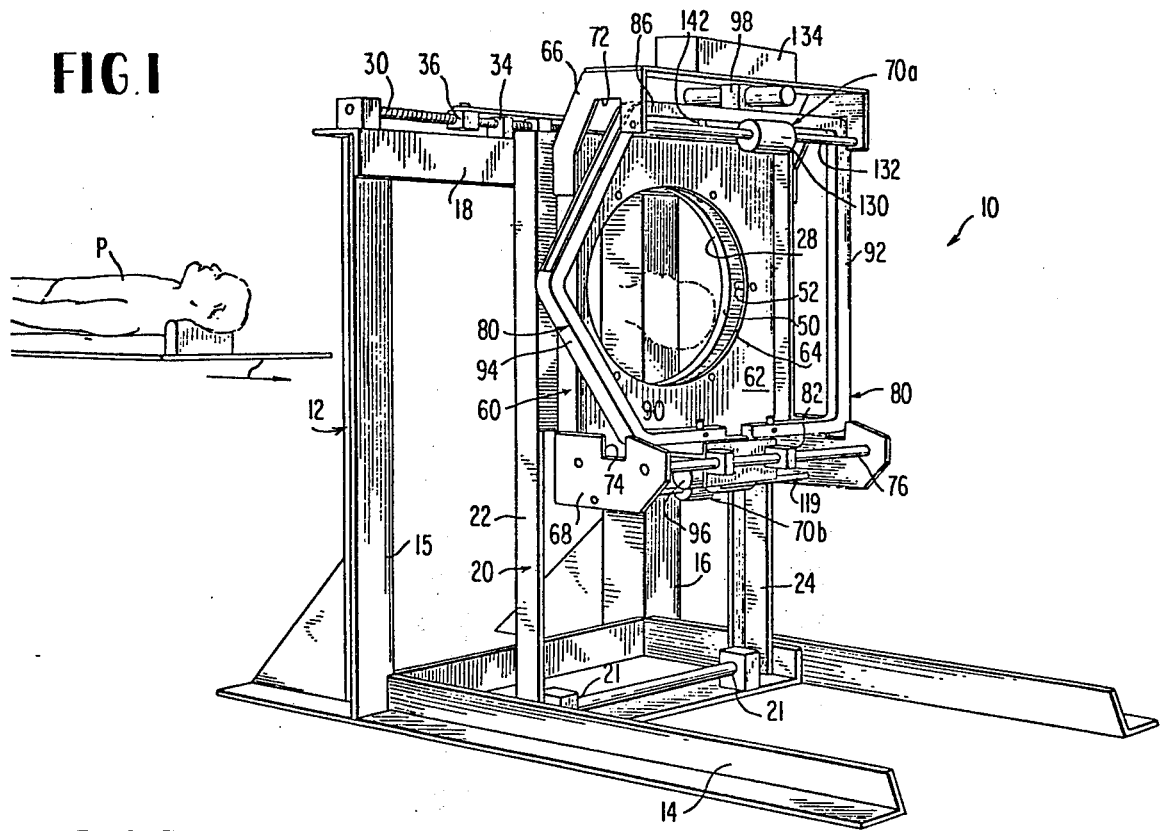
FIG. 1 is a diagrammatic perspective view of the invention showing its general arrangement and construction.

Referring now to the drawings wherein like parts are indicated by like numerals, the numeral 10 generally indicates the scanning apparatus of this invention. The apparatus has as its principal supporting mechanism, a framework 12 supported by a ground-engaging supporting by the numeral 14.

In addition to base 14, the framework 12 consists of first and second uprights 15 and 16 having a cross-member 18 extending between their upper ends. A carrier frame 20 is disposed immediately in front of frame 16 and is pivotally mounted at points 21 to base member 14. The particular pivot mounting means is any convenient structure providing it permits carrier frame 20 to tilt as least 10° toward frame 14 and approximately 20° therefrom. The desired extent of tilting is illustrated in dotted lines in FIG. 4.

The carrier frame 20 includes a pair of uprights 22 and 24 to which a housing 26 is secured. The housing 26 is provided with an opening 28 sufficiently large to readily accommodate a patient represented by the letter P on the drawings.

Disposed on the upper surface of cross-beam 18 is a drive screw 30 which is rotated by a motor 32. An unthreaded center of screw 30 is rotatably supported in block 34 which is affixed to cross-beam 18. The threads on opposite sides of block 14 are formed in opposing directions. This causes blocks 36 and 38 to move in opposite directions toward or away from each other, depending upon the direction of rotation of shaft 30.

The blocks 36 and 38 are interconnected to the upper end of frame 20 by a pair of crossed bars 40 and 42 which have first ends, respectively, and rotatably connected to blocks 36 and 38 and their other ends, respectively, and rotatably connected to pins 44 and 46 located at the top of frame 20. Therefore, it can be seen that a rotation of drive shaft 30 will cause the framework 22 to tilt about pivot points 21 as determined by the degree of extension in the scissor-arranged bars 40 and 42.

Disposed interiorly of plate 26 are a plurality of circumferentially arranged bearing members 48 (FIG. 6) which rotatably mount, and position, a ring 50. Extending forwardly of ring 50 are a plurality of threaded studs 52. As best seen in FIG. 10, the ring 50 also has a flange 54. The flange 54 is formed with gear teeth 55 which mate with a drive gear 56. Gear 56 is rotated by the motor 58. Thus, motor 58 is the power source for rotating ring 50.

Figure 3:
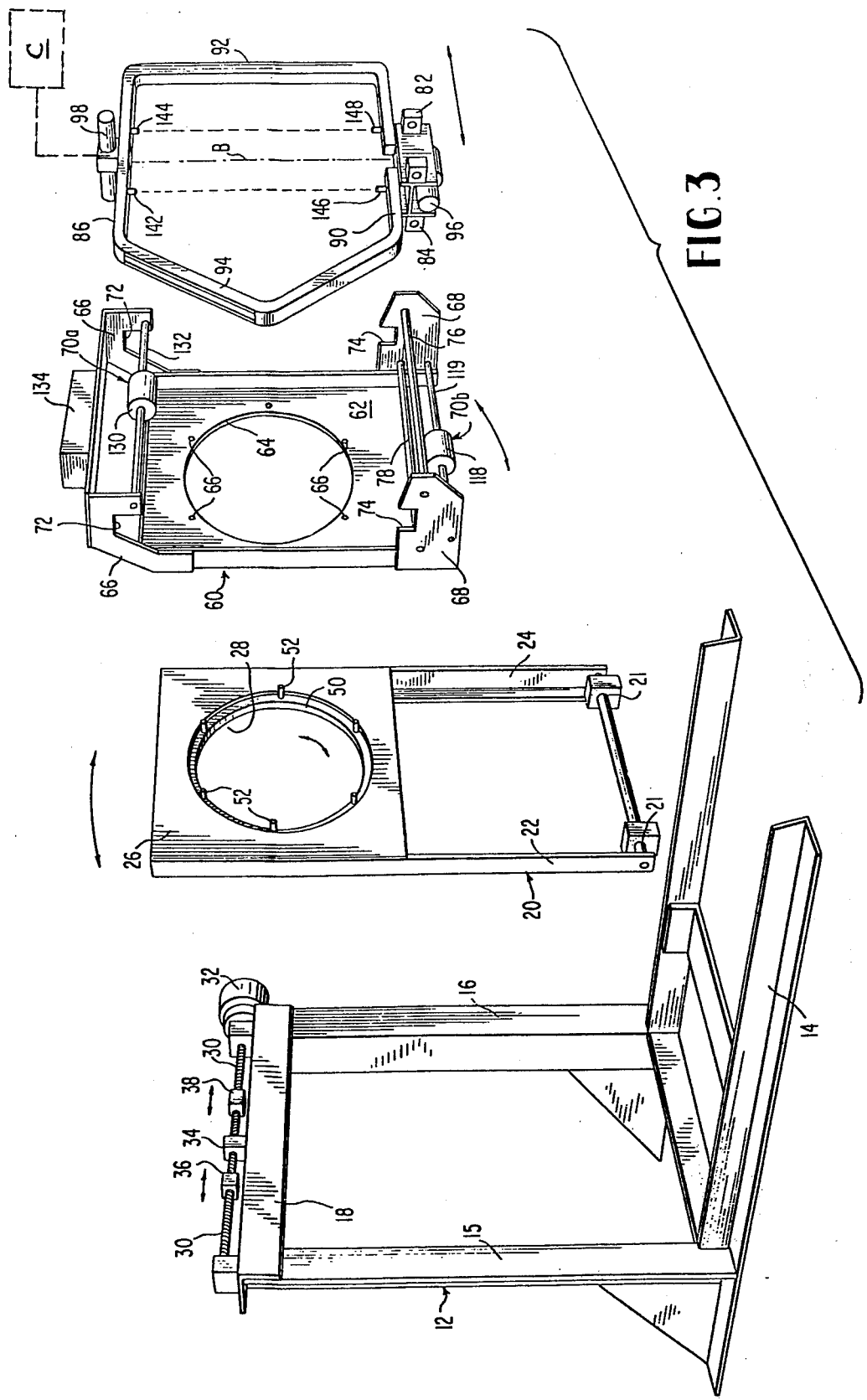
FIG. 3 is an exploded perspective of the major elements of FIG. 1.

The rotating frame 60 includes a plate 62 having an opening 64 generally coextensive in size and axial placement with the opening 28 as defined more particularly by the inner circumference of ring 50. Disposed about the opening 64 are a series of apertures 66 which receive the aforementioned threaded studs 52. This arrangement causes the frame 60 to rotate with ring 50. Affixed to the upper side of framework 60 is an upper bracket 66 and affixed to the lower side of framework 60 is a lower bracket 68. The brackets 66 and 68 carry counterweight assemblies 70a and 70b therebetween. The lower edges of upper brackets 66 and the upper edges of brackets 68 are formed, respectively, with grooves 72 and 74 to receive a transversely moving frame 80. The lower bracket 68 has trans- verse supporting rods 76 and 78 which slidably receive the transverse frame 80 via blocks 82 and 84 which are slidably received thereon. The transverse moving framework 80 has an upper side 86, a base 90, a first side 92, and a second side 94. Side 94 is slightly peaked as best seen in FIG. 3. In the described embodiment, a radiation source 96 is a conventional X-ray machine capable of producing a narrow ribbon or beam indicated on the drawings by the letter B. On the upper side 86 of the frame is a crystal detector 98 adapted to receive the beam B and convert it into electronic signals which are thereafter processed into the desired display by a computer C. In this description, the computer and wires leading thereto are shown diagrammatically. However, suitable computer programming used for tomography scanning of the type performed by this invention is discussed in an article, *Proceedings, National Academy of Science USA* Volume 68, No. 9 pages 2236–2240 September 1971).

FIGS. 6 through 9 best disclose the translational or transverse movement of the X-ray machine and the collector. A stepping motor 102 is mounted on a bracket 104. The output of motor 102 is fed to a gear reducer 106 which in turn rotates a pulley 108. About pulley 108 is a drive tape or belt 110 to which frame 80 is connected. The weight is assumed by rods 76 and 78. A counterweight 118 of counterweight assembly 70b is carried by rod 119. Counterweight 118 is secured to a cable 120 which in turn is supported by pulleys 112 and 114 as best shown in FIG. 9. Cable 120 is connected to the X-ray carrying frame 80 by connector 116. Therefore, as the X-ray 96 is moved in one direction, the counterweight 118 moves in the other.

Another series of pulleys 122 and 124 are mounted near the top of the assembly and have a cable 126 extending thereabout. The detector 98 is secured to tape 126 via the bracket 128. This assembly also includes a movable counterweight 130 slidably received on the rod 132. A stationary counterweight 134 is provided to counterbalance the relatively heavy X-ray mechanism attached to the lower side of frame 80.

Figure 2:
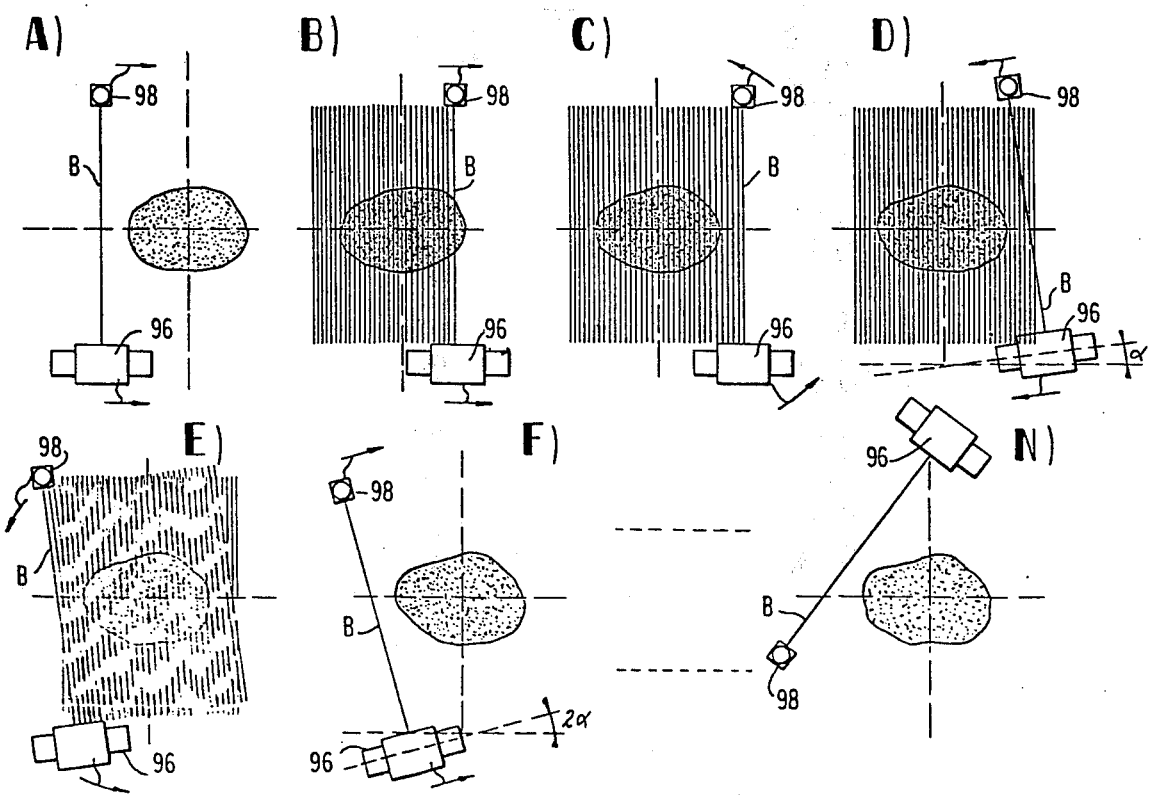
FIG. 2 is a series of diagrams illustrative of the tomographic scanning pattern taken during operation.

A common use for this invention is to precisely locate and determine the size and shape of a brain tumor. In FIG. 2 there is illustrated the mechanical movements of the X-ray source and the detector as they examine the interior of the skull portion of a patient. The patient is located within the opening in framework 80. The physician, in many instances, knows the approximate plane of the tumor. A marking can be placed on the exterior of the patient's head. The patient is then accurately located within the framework 80 by "sighting" through the elongated slot 95 in side 94.

The motor 102 then moves the transverse framework laterally as shown in FIGS. 2B and 2C in order to take the series of scans diagrammatically depicted. After the entire cranium has been examined in this way, frame 60 is rotated angularly counterclockwise (as seen in FIG. 2) to the position shown in FIG. 2D. The frame 60 is rotated a selected amount from 1° to 6° as indicated by the angle $\alpha$. The X-ray source and collector move transversely through for another series of scans, as seen in FIG. 2E. As seen in FIG. 2F the rotating frame is rotated again to a two $\alpha$ position where the series of scans is again taken. This sequence continues until the rotating frame has been rotated 180°. The computer receives the information required for it to make a pictorial or other type of display in a single particular plane. After one plane is completed, the apparatus is returned to the start position of FIG. 2A. The patient is moved forwardly approximately two to six millimeters and another series of scans is taken in the conventional tomographic scanning manner.

In the event it is desired to examine some other portion of the body such as the kidneys or other trunk organs, the entire assembly can be tilted by operating the motor 32 as hereinbefore described. The purpose of tilting is to locate the plane of the scanning assembly normal to a center axis of the organ under investigation.

It should be understood, of course, that once the patient is positioned for a particular scanning sequence as shown in FIG. 2, the motors operate in accordance with a selected sequence which requires no further mechanical operation by the operator. In other words, the motor 58 through a series of conventional switches, is set to move the ring 50 at 1° to 6° intervals. The motor 102 is selected to take a beam scan from 0 to 6 mm. The combination of settings is determined from the medical requirements of the particular patient under diagnosis. Additionally, the number of planes required is likewise determined from the medical requirements.

Figure 11A:
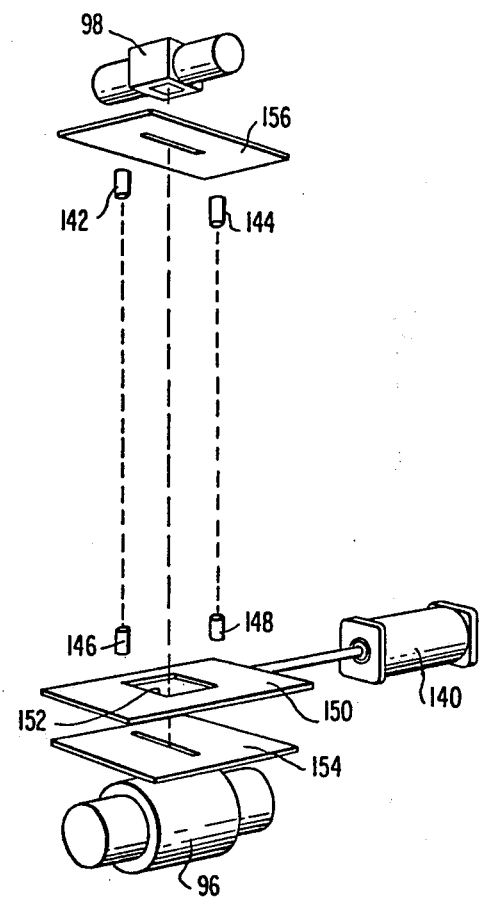
FIGS. 11a – 11c are diagrammatic sketches showing operation of the shutter mechanism.
Figure 11B:
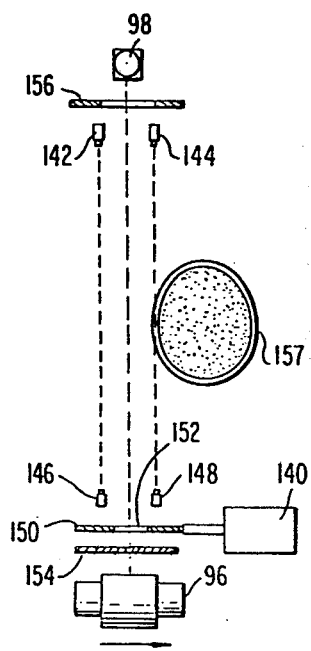

The shutter arrangement and its operation is shown in FIGS. 11A and 11B. As seen, a solenoid 140, secured to frame 80, is disposed between the X-ray source 96 and the crystal detector 98. On the upper side 86 of transverse framework 80 are a pair of photocells 142 and 144 located directly above a pair of light sources 146 and 148 on the bottom side 90. The solenoid 140 carries a shutter 150 of copper or the like having a beam-receiving opening 152 therein. A collimator 156 is disposed immediately below the crystal detector 98. The beam-receiving slots in collimator 154 and 156 are, of course, in line with beam B. The purpose of shutter 150 is to interrupt the beam until such times as the patient approaches beam B. The photocells and the lights are movably mounted to their respective mounting members.

Figure 11C:
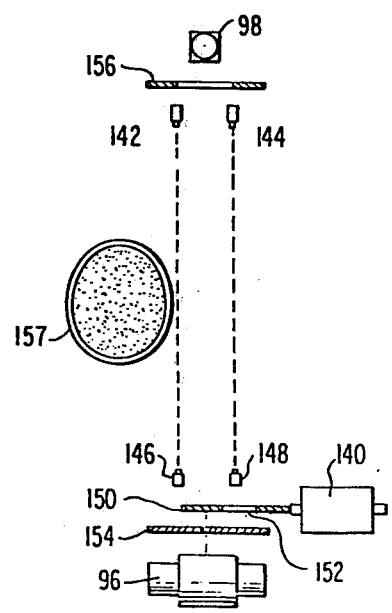

A band 157 of X-ray transmitting material through which X-rays will pass (but opaque or at least translucent to light) is placed about the patient's body at the section where the X-ray picture is to be taken. The band 157 because of the thickness extending beyond the edge of the patient, causes the solenoid 140 to energize just prior to the X-ray entering to thereby open the beam path. FIG. 11B shows the disposition as band 157 just interrupts the beam between light source 148 and photocell 144. This will activate the solenoid and move the slot 150 to the position shown, i.e., where the collimator slots and the slot 152 are along a common axis. In FIG. 11C the disposition is shown wherein the frame 80 is approaching the end of its translation movement for that portion of the body under investigation. As the band 157 opens the light between source 146 and detector 142, the solenoid is de-energized and a solid section of shutter will interrupt the beam between the X-ray source and detector 98. Thus, using the patient's band, the shutter is signaled to open slightly in advance and slightly after the patient tissue enters the X-ray path. The shutter is closed when the patient is not in the path of the X-ray beam. Any simple electrical circuitry can be utilized to obtain this sequence. The band serves the additional service of cutting down the X-ray intensity just prior to the time the X-rays enter the body of the patient. In other words as the X-ray passes through the air it is of such high intensity that the electronic control equipment must adjust to this transmission. With the use of the band, the transition takes place outside of the patient's body. Therefore, the equipment is fully adjusted prior to the time that the X-rays enter the body. The band may be of any suitable material which would accomplish the intended purpose, however, in preferred embodiments, foam rubber or foam plastic or a gel have been found to be suitable.

The patient is brought to the apparatus by way of a mobile cot 160 and removed via the mobile cot 162. The patient is supported by the table 164 while being diagnosed. Table 164 is comprised of a platform 166 by a pair of forward legs 168 and rearward legs 170. The legs are pivotally mounted at their upper ends to the table 164 and at their lower ends, pivotally mounted to base 14. An intermediate strut 172 is pivotally connected to one of the forward legs and to one of the rear legs intermediate their lengths. Strut 172 is also pivotally connected to upright 22 intermediate its length. Of course, a second strut can be likewise mounted to the legs and upright 24 on the longitudinal side of the support, not shown, in FIGS. 3 and 4. Through this parallelogram arrangement the platform 166 is automatically lowered when framework 20 is tilted.

A patient-carrier, stretcher-like member 180 is slidably received on platform 166 for longitudinal movement with respect thereto. Anti-friction elements can be disposed therebetween. The plate 180 is formed with a rack 184 which is formed in the base of a groove extending the longitudinal length of member 180 and this rack is adapted to be engaged by the output pinion 186 of the stepping motor 188. This sliding arrangement permits the patient to be accurately moved the selected distance, usually from 2 to 6 mm., between the tomographic scans.

In a general manner, while there has been disclosed an effective and efficient embodiment of the invention, it should be well understood that the invention is not limited to such an embodiment, as there might be changes made in the arrangement, disposition, and form of the parts without departing from the principle of the present invention as comprehended within the scope of the accompanying claims.

I claim:

1. An improved diagnostic medical machine utilizing beams of radiation of small cross-sectional diameter for the purpose of mapping cross-sections of a patient's body in combination with a computer, comprising,
   a table for supporting a patient in a generally horizontal position,
   a generally vertical first frame having an opening therethrough of a size sufficiently large to permit the patient and said table to move therethrough,
   a carrier frame rotatably mounted on said first frame and having a second opening generally coextensive with said first opening,
   a narrow beam from a radiation source,
   a collector to receive said beam of radiation,
   first means mounting said source and collector to said carrier frame for translational movement with respect to said carrier and to carry said beam of radiation across said patient's body,
   second means for rotating said carrier about said patient's body,
   a shutter means disposed between said source and the patient's body and interrupting said beam, and
   means to move said shutter from the path of said beam just prior to its approach to said patient's body as it is carried by said first means.

2. The invention of claim 1 and including a pair of collimators, one between said radiation source and said patient and the other between said collector and said shutter.

3. The invention of claim 1 wherein said means to move is a solenoid mounted on said first frame.

4. The invention of claim 3 wherein said band is of foam rubber.

5. The invention of claim 3 wherein said means to move further includes an X-ray absorbent band about said patient's body.

6. The invention of claim 5 wherein said band is opaque to light.

7. the invention of claim 5 wherein said band is of foamed plastic.

8. The invention of claim 1 wherein said shutter comprises an apertured plate.

9. The invention of claim 8 wherein said plate is of copper.

10. The invention of claim 1 wherein said means to activate said beam includes a system for detecting the presence of the patient, said system including an X-ray transmitting element on said patient.

11. The invention of claim 10 wherein said X-ray transmitting element comprises a light-opaque band about said patient's body.

12. The invention of claim 11 wherein said band is of a foamed rubber material.

13. The invention of claim 11 wherein said band is of a foamed plastic material.

14. An improved diagnostic medical machine utilizing beams of radiation of small cross-sectional diameter for the purpose of mapping cross-sections of a patient's body in combination with a computer, comprising,
- a table for supporting a patient in a generally horizontal position,
- a generally vertical first frame having an opening therethrough of a size sufficiently large to permit the patient and said table to move therethrough,
- a carrier frame rotatably mounted on said first frame and having a second opening generally coextensive with said first opening,
- a narrow beam from radiation source,
- a collector to receive said beam of radiation,
- first means mounting said source and collector to said carrier frame for translational movement with respect to said carrier and to carry said beam of radiation across said patient's body,
- second means for rotating said carrier about said patient's body,
- means to activate said beam just prior to its approach to the patient's body as it is carried by said first means.

15. An improved diagnostic medical machine utilizing beams of radiation of small cross-sectional diameter for the purpose of mapping cross-sections of a patient's head in combination with a computer, comprising,
- a table for supporting a patient in a generally horizontal position,
- a narrow beam from a radiation source,
- a collector to receive said beam of radiation,
- means mounting said source and collector for relative movement with respect to said table,
- beam energizing means,
- an X-ray transmitting element on said patient's body; and
- means responsive to said X-ray transmitting element for activating said energizing means.

16. The invention of claim 15 wherein said X-ray transmitting element comprises a light-opaque band about said patient's body.

17. The invention of claim 15 wherein said band is of a foamed rubber material.

18. The invention of claim 15 wherein said band is of a foamed plastic material.

* * * * *